United States Patent [19]

Ponpipom et al.

[11] 4,386,026

[45] May 31, 1983

[54] CELL-SPECIFIC GLYCOPEPTIDE LIGANDS

[75] Inventors: Mitree M. Ponpipom, Branchberg; Robert L. Bugianesi, Colonia; James C. Robbins, Monmouth Junction; Tsung-Ying Shen, Westfield, all of N.J.

[73] Assignee: Merck & Co., Inc., Rahway, N.J.

[21] Appl. No.: 255,416

[22] Filed: Apr. 20, 1981

[51] Int. Cl.³ .................... C07C 103/52; C08B 37/00; C07H 11/00
[52] U.S. Cl. ................ 260/112.5 R; 536/53; 536/18.7; 536/54; 536/115
[58] Field of Search ............. 260/112.5 R; 536/53, 536/18, 115

[56] References Cited

U.S. PATENT DOCUMENTS

| | | | |
|---|---|---|---|
| 3,226,379 | 12/1965 | Steyermark et al. | 536/53 |
| 3,859,337 | 1/1975 | Herz et al. | 536/53 |
| 4,120,953 | 10/1978 | Nair et al. | 536/53 |
| 4,175,073 | 11/1979 | Carlsson et al. | 536/1 |
| 4,195,128 | 3/1980 | Hildebrand et al. | 536/1 |
| 4,223,013 | 9/1980 | Hu et al. | 260/112.5 R |
| 4,241,053 | 12/1980 | Tsujihara | 536/53 |
| 4,259,233 | 3/1981 | Carrico et al. | 260/112.5 R |

OTHER PUBLICATIONS

Biol. Abstr. 68, 24673.
Biol. Abstr. 67, 27708.
Biol. Abstr. 69, 34308.
Chabala et al., Carbohydrate Research, 67, (1978), pp. 55-63.
Ponpipom et al., Canadian Journal of Chemistry, 58, pp. 214-220 (1980).
Mauk et al., Science, 207, pp. 309-311 (1980).
Mauk et al., Proc. Natl. Acad. Sci. U.S.A., 77, pp. 4430-4434 (1980).
Martodam et al., Proc. Natl. Acad. Sci. U.S.A., 76, pp. 2128-2132 (1979).
Ashwell et al., Adv. Enzmol., 41, pp. 99-129 (1974).
Gregoriadis, G., Nature, 265, pp. 407-411 (1977).

*Primary Examiner*—Delbert R. Phillips
*Attorney, Agent, or Firm*—Thomas E. Arther; Mario A. Monaco

[57] ABSTRACT

Cell-specific ligands comprising conjugates of saccharides and amino acids or peptides are synthesized from amino acids such as ornithine, lysine, peptides such as dilysine, diornithine or oligolysine and selected saccharides having reactive functional groups protected by appropriate blocking groups. Such glycopeptides are useful as tissue specific substances, which when coupled with bioactive materials through metabolizable or hydrolyzable linkages, deliver such bioactive materials to the selected site. In this manner, antiinflammatory drugs such as dexamethasone are linked through a metabolizable or hydrolyzable linkage and on administration to an animal suffering from inflammatory disease carries the drug to the site of inflammation for intracellular release. Other examples include the macrophage ligand $N^2$-$N^2$, $N^6$-Bis-[3-($\alpha$-D-mannopyranosylthio)propionyl]-6-lysyl-$N^6$-[3-($\alpha$-D-mannopyranosylthio)propionyl]-L-lysine, 5, which when coupled to $\beta$-glucocerebrosidase, can deliver the enzyme selectively to kupffer cells. This is useful in the enzyme replacement therapy of Gaucher's disease.

8 Claims, No Drawings

CELL-SPECIFIC GLYCOPEPTIDE LIGANDS

BACKGROUND OF THE INVENTION

The use of drugs for therapeutic purposes would be greatly enhanced by a method which would introduce them selectively into those cells where the pharmacological action is needed. Several approaches to accomplish this purpose have been investigated. Two groups of investigators; J. C. Chabala and T. Y. Shen, *Carbohyd. Res.*, 67, 55 (1978); M. M. Ponpipom, R. L. Bugianesi, and T. Y. Shen, *Canad. J. Chem.* 58, 214 (1980), M. R. Mauk, R. C. Gamble and J. D. Baldeschwieler, *Science* 207, 309 (1980); *Proc. Natl. Acad. Sci. U.S.A.* 77, 4430 (1980), have synthesized and incorporated glycolipids into liposomes and studied their distribution in vivo showing the importance of carbohydrates as cell-surface determinants.

Other investigators have studied the use of human albumin microspheres covalently coupled to succinoyl-Ala-Ala-Pro-ValCH$_2$Cl which is an active site-directed inhibitor of human leukocyte elastase. These investigators reported that such conjugates directed the inhibitor to the lungs when administered intravenously in rats, R. R. Martodam, D. Y. Twumasi, I. E. Liener, J. C. Powers, N. Nishino and G. Krejcarek, *Proc. Natl. Acad. Sci. U.S.A.* 76, 2128 (1979). Earlier work of G. Ashwell and A. Morell, *Adv. Enzmol.* 41, 99 (1974) demonstrated that exposed sugar residues in glycoproteins serve as determinants for in vivo (i.e. clearance) and in vitro (i.e. uptake) recognition.

Many other selective drug delivery systems have been described, G. Gregoriadis (Ed.) "Drug Carriers in Biology and Medicine", Academic Press 1979; *Nature* 265, 407 (1977) including binding a drug or dose of radioactive atom to tumor specific antibodies. In addition, deoxynucleic acid (DNA) has been used as a carrier for antitumor drugs such as daunorubicin, adriamycin and ethidium bromide.

These methods, although useful in certain cases have some problems. In some cases the targeting is too imprecise and the payload too small. Use of DNA and liposomes as carriers also has certain problems related to potential toxicity and pharmaceutical requirements.

The present invention provides a tissue specific ligand which is chemically bound to a bioactive agent for administration and which is specific in its targeting ability. The ligand is carefully selected to avoid toxicity or side effects and is relatively easy to prepare and standardize for in vivo administration.

DESCRIPTION OF THE INVENTION

The invention in the present instance includes a composition for chemically binding drugs or other bioactive substance for administration and delivery of the bioactive substance to a preselected tissue site.

The composition of the present invention comprises a relatively low molecular weight chemical conjugate comprising a saccharide moiety preferably including 1-4 linked monosaccharide units functionaly linked to a polyfunctional backbone which in turn is *optionally* linked to a biologically active moiety for delivery to specific tissues for intracellular release. The polyfunctional backbone comprises from 1 to 4 alkyl, alkenyl, aryl, or aralkyl residues linked through a functional substituent selected from O—; S—; NH—; —S—S—;

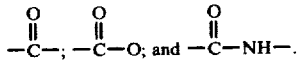

These compositions are symbolically represented as follows:

$[Sa]_n\text{—}B_n\text{—}[BA]_n$ wherein Sa is a saccharide comprising from 1 to 4 linked monosaccharide units.

B is a polyfunctional backbone and spacer arm moiety represented by —X$n$(W)$_n$Y$_n$— wherein X and Y are the same or different and are selected from —O—; —S—; —NH—; —S—S—;

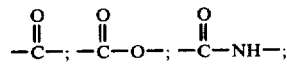

W is selected from lower alkyl, lower alkenyl, aryl, or aralkyl e.g. phenyl or benzyl;

n is an integer of from 1 to 4 inclusive and BA represents a biologically active substance or hydrogen.

The saccharide employed in the composition of the present invention is a saccharide comprising from 1–4 monosaccharide units containing for example as monosaccharide units D-Man(D-mannose), D-Gal(D-galactose), L-Fuc(L-fucose), D-GlcNAc(2-acetamido-2-deoxy-D-glucose), NeUNAc(N-acetylneuraminic acid), D-Glc(D-glucose), GalNAc(2-acetamido-2-deoxy-D-galactose) and substituted derivatives thereof.

Such conjugates, wherein BA represents hydrogen, are saccharide containing ligands which can be reversibly linked to a biologically active substance for selective delivery to tissues and organs for intracellular release. The biologically active substances include enzymes, hormones, genetic fragments, antibiotics, and radioactive isotopes.

The composition of the present invention is preferably a synthetic glycopeptide which can be chemically bound by means of a hydrolyzable or metabolizable linkage to a drug or other bioactive substance.

Preferred compositions of the present invention include novel glycopeptides comprising a compound including a peptide moiety selected from one or more amino acids such as serine, cysteine, ornithine, diornithine, lysine, dilysine and oligolysines or a mixture of these functionalized amino acids; a saccharide moiety including a mono-, di- or oligosaccharide or thiosaccharide moiety and an alkylenecarbonyl linking function, said linking carbonyl function forming an amide linkage with the amine groups of said peptide moiety and a hemiacetal or a thiohemiacetal linkage with the aromatic carbon of said saccharide moiety and preferably containing from 1–8 carbon atoms.

Thus, the composition prepared in accordance with the present invention include for example glycopeptides derived from ornithine, lysine, dilysine or an oligolysine of the general formula:

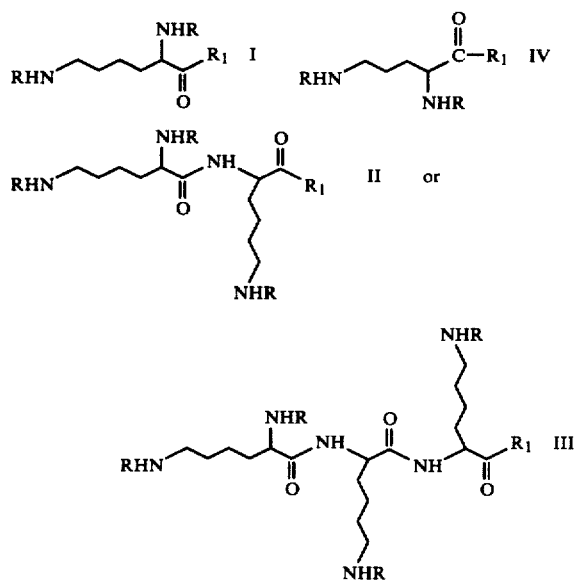

wherein R is a saccharide compound selected from the group consisting of

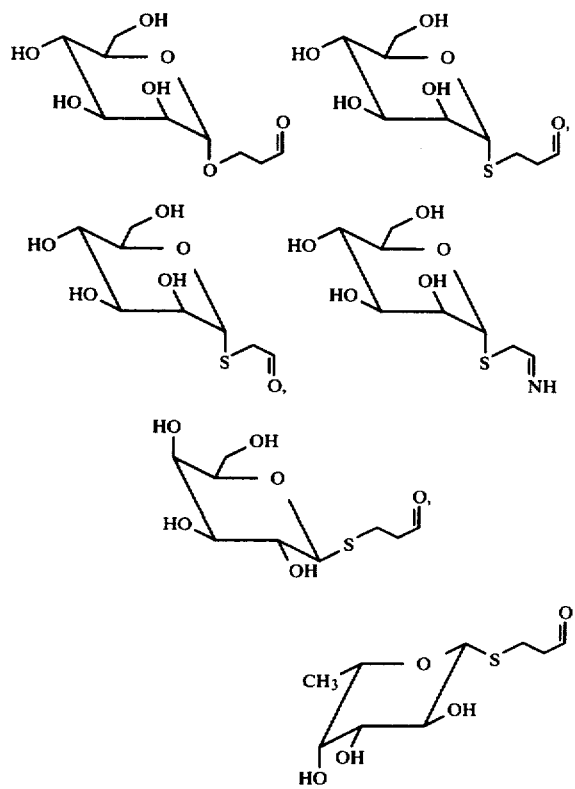

and $R_1$ is selected from the group consisting of hydroxyl and $NHR_2$ in which $R_2$ is 6-aminohexyl, and acid addition salts thereof.

Although the compounds illustrated hereinabove disclose glycopeptide compounds in which the saccharide moiety is linked to the peptide through a sulfur linkage and a methylene or ethylene chain connected to the amide linkages, applicant includes as part of the subject invention the corresponding compounds in which the sulfur linkage is replaced by oxygen. It is further noted that the alkylene chain in addition to methylene and ethylene can include alkylene chains preferably containing from 1-8 carbon atoms.

Preferably the compositions of the subject invention are glycopeptides of ornithine, lysine or dilysine or an oligolysine and a selected sugar residue derived from galactose, fucose, mannose and other saccharides including di- and oligosaccharides. Especially preferred compositions are derivatives of ornithine, dilysine, lysine and oligolysine selected from $N^2$-{$N^2,N^6$-bis[3-($\alpha$-D-mannopyranosylthio)propionyl]-L-lysyl}-$N^6$-[3-($\alpha$-D-mannopyranosylthio)propionyl]-L-lysine (5); N-6-aminohexyl-$N^2$-{$N^2,N^6$-bis[3-($\alpha$-D-manopyranosylthio)propionyl-L-lysyl}-$N^6$-[3-($\alpha$-D-mannopyranosylthio)propionyl]-L-lysinamide trifluoroacetate salt (7); $N^2,N^6$-bis[3-($\alpha$-D-mannopyranosylthio)propionyl]-L-lysine (12); $N^2$-{$N^2,N^6$-bis[1-imino-2-($\alpha$-D-mannopyranosylthio)ethyl]-L-lysyl}-$N^6$-[1-imino-2-($\alpha$-D-mannopyranosylthio)ethyl]-L-lysine (17); $N^2,N^6$-bis[3-($\alpha$-D-mannopyranosylthio)propionyl]-D-lysine (14); $N^2$-{$N^2$-{$N^2,N^6$-bis[3-($\alpha$-D-mannopyranosylthio)propionyl]-L-lysyl}-$N^6$-[3-($\alpha$-D-mannopyranosylthio)propionyl]-L-lysyl}-$N^6$-[3-($\alpha$-D-mannopyranosylthio)propionyl]-L-lysine (16); $N^2$-{$N^2,N^6$-bis[3($\beta$-D-galactopyranosylthio)propionyl]-L-lysyl}-$N^6$-[3-($\beta$-D-galactopyranosylthio)propionyl]-L-lysine (20); N-6-aminohexyl-$N^2$-{$N^2,N^6$-bis[3-($\beta$-D-galactopyranosylthio)propionyl]-L-lysyl}-$N^6$-[3-($\beta$-D-galactopyranosylthio)propionyl]-L-lysinamide trifluoroacetate salt (22); $N^2$-{$N^2,N^6$-bis[3-($\beta$-L-fucopyranosylthio)propionyl]-L-lysyl}-$N^6$-[3-($\beta$-L-fucopyranosylthio)propionyl]-L-lysine (26); $N^2$-{$N^2,N^6$-bia[($\alpha$-D-mannopyranosylthio)acetyl]-L-lysyl}-$N^6$-[($\alpha$-D-mannopyranosylthio)acetyl]-L-lysine (32); N-6-aminohexyl-$N^2,N^6$-bis[3-($\alpha$-D-mannopyranosylthio)propionyl]-L-lysinamide trifluoroacetate salt (34); $N^2,N^5$-[bis[3-($\alpha$-D-mannopyranosylthio)propionyl]-L-ornithine (37); $Man^9$-$Lys^8$ (39); $N^2$-{$N^2,N^6$-bis[3-($\alpha$-D-mannopyranosyl)propionyl]-L-lysyl}-$N^6$-[3-($\alpha$-D-mannopyranosyl)propionyl]-L-lysine (41).

The compositions of the present invention are prepared by reactions of ornithine, lysine, dilysine, or an oligolysine with w-carboxyalkyl per-0-acylglycosides or -1-thioglycosides that involve amide-bond formation. The carbohydrates selected can be mannose, galactose, fucose or other saccharides including di- and oligosaccharides.

The corresponding compounds in which the amide linkage is replaced by an amidine linkage are prepared by reaction of ornithine, lysine, dilysine, or oligolysine with 2-imino-2-methoxyethyl 1-thioglycosides of mannose, galactose, fucose or other saccharides including di- and oligosaccharides. These intermediates are illustrated in the case of L-lysine by the following formula:

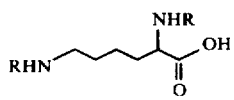

in which R is illustrated as follows:

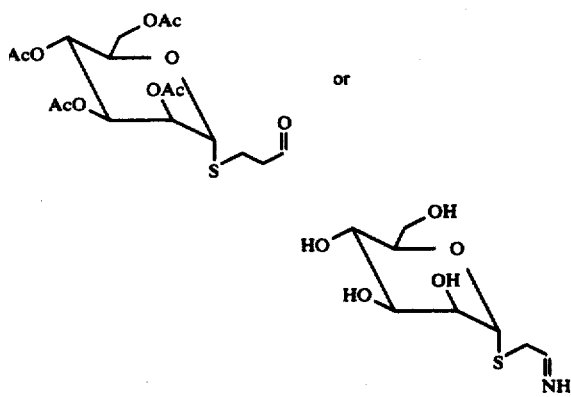

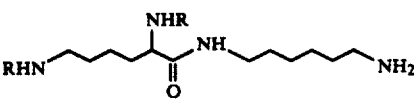

Compounds of the type in which the glycopeptide contains a terminal amino function are readily prepared from the corresponding glycopeptide having a free carboxyl group by reaction of the said glycopeptide with a monoblocked hexylamine, e.g., 6-t-butyloxycarbonylaminohexylamine, in the presence of a condensing agent such as dicyclohexylcarbodiimide followed by hydrolysis of the 6-(butyloxycarbonyl) function and resultant production of an intermediate compound of the formula

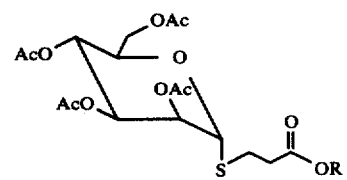

and the corresponding oligolysine derivatives wherein R is as described above.

In addition to the novel glycopeptide composition described hereinabove the present invention also includes adducts of said glycopeptides with known bioactive substances. Said adducts are preferably formed by amidation of a terminal amine function of the glycopeptide compound to form an amide which is readily hydrolyzed intracellularly or is formed as an ester with a free carboxyl function of the glycopeptide compound.

The following structural formulas identify structurally compounds of our invention which are disclosed in the examples which follow immediately thereafter.

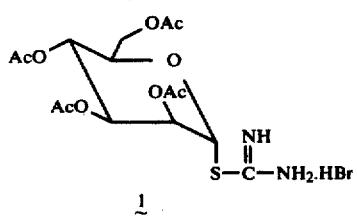

1

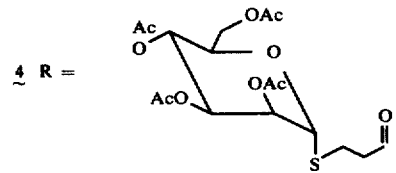

2 R = H
3 R = C$_6$H$_4$NO$_2$—p

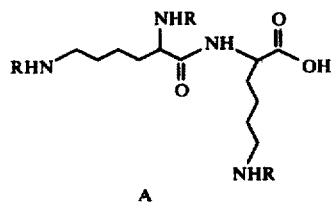

A

4 R = 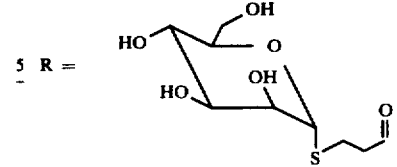

5 R = 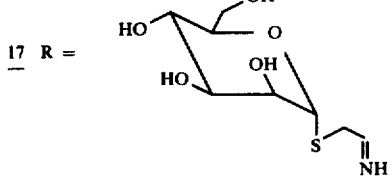

17 R = (structure)

31 R = 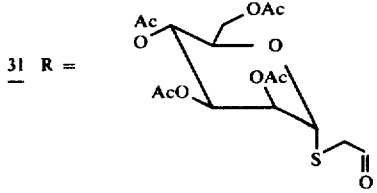

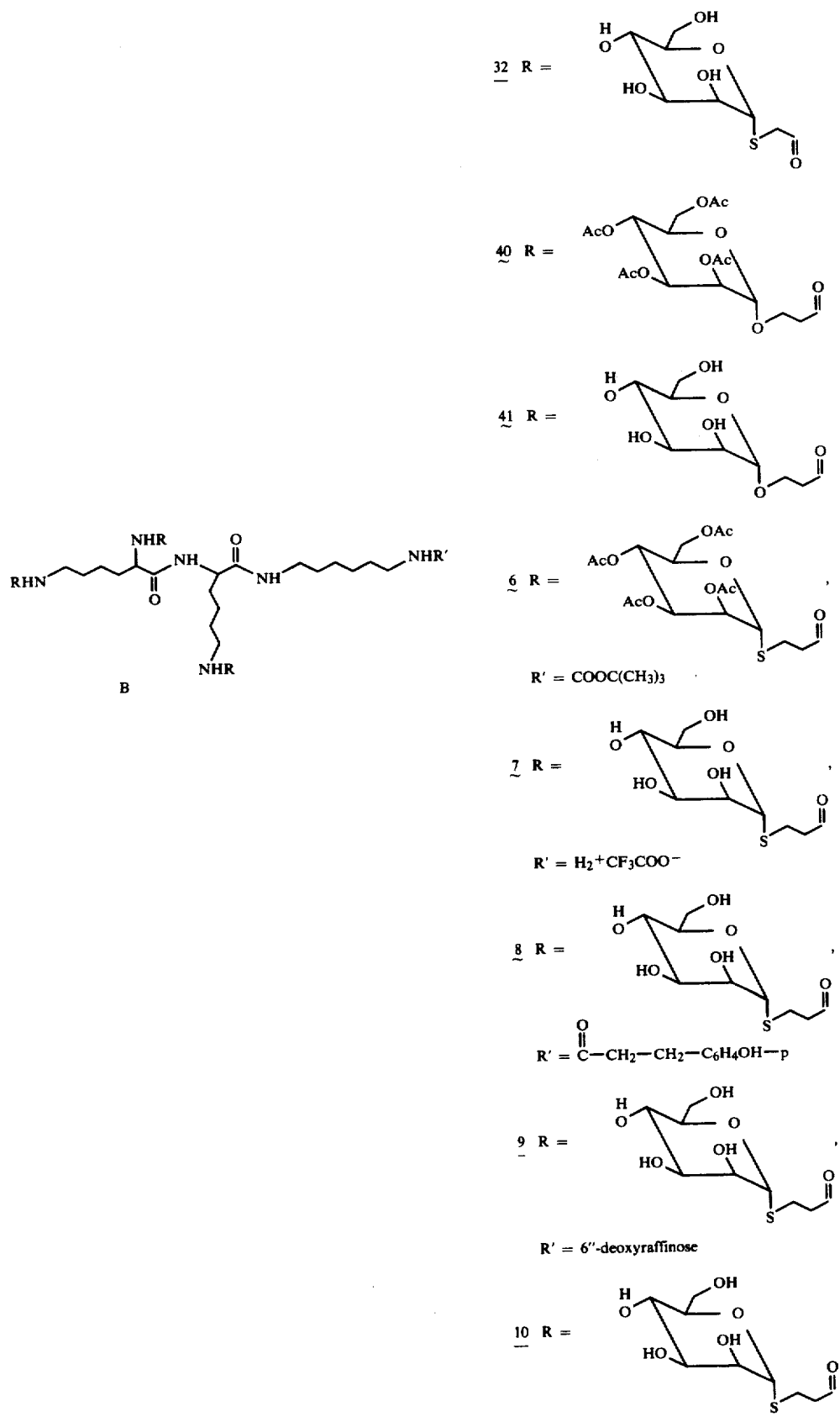

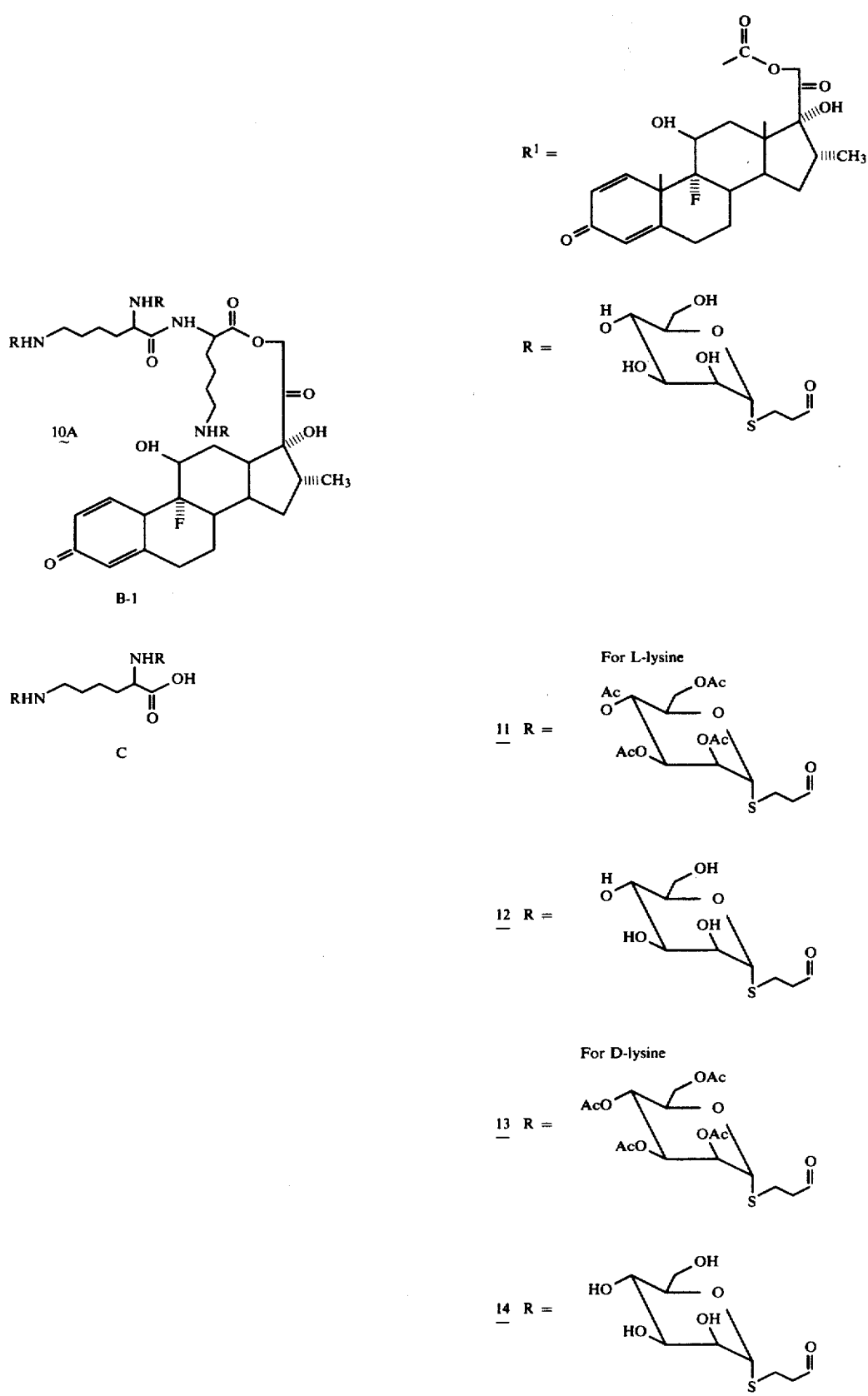

-continued
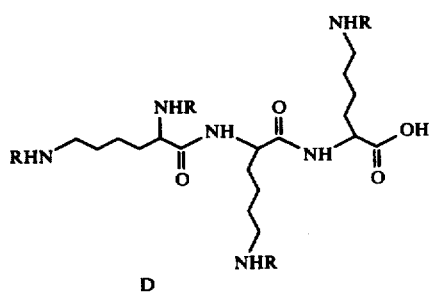
D
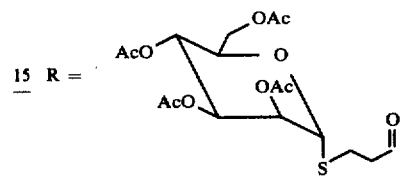
15 R =
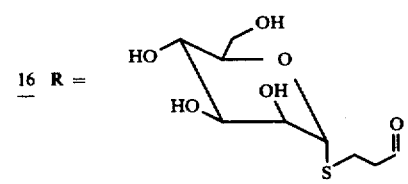
16 R =
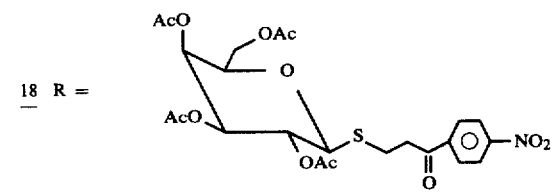
18 R =
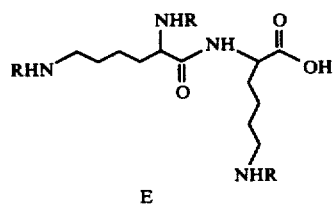
E
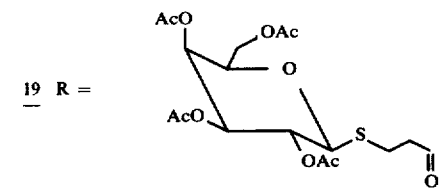
19 R =
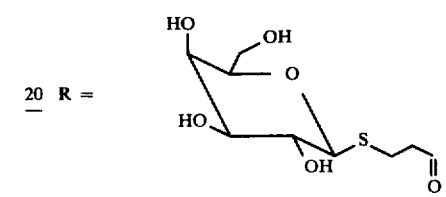
20 R =
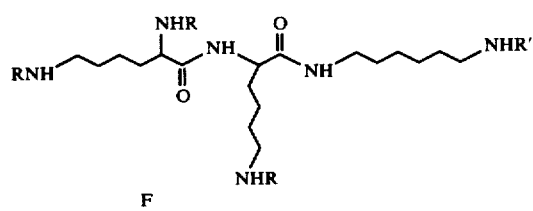
F
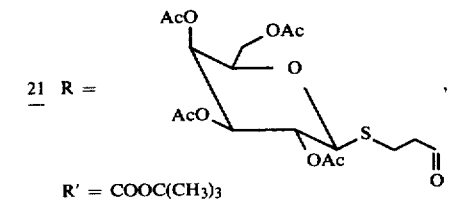
21 R =
R' = COOC(CH₃)₃
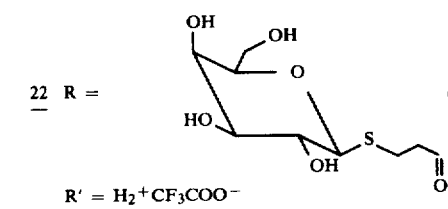
22 R =
R' = H₂⁺CF₃COO⁻

-continued

23 R = H
24 R = C₆H₄NO₂—p

25 R = [sugar with CH₃, OAc groups, S-CH₂-CHO]

26 R = [sugar with CH₃, OH groups, S-CH₂-CHO]

27 R = [sugar with Ac, OAc groups, S-CH₂-CHO]

28 R = [sugar with OH groups, S-CH₂-CHO]

29 R = H
30 R = C₆H₄NO₂—p

33 R = [sugar with Ac, OAc groups, S-CH₂-CHO]

R' = COOC(CH₃)₃

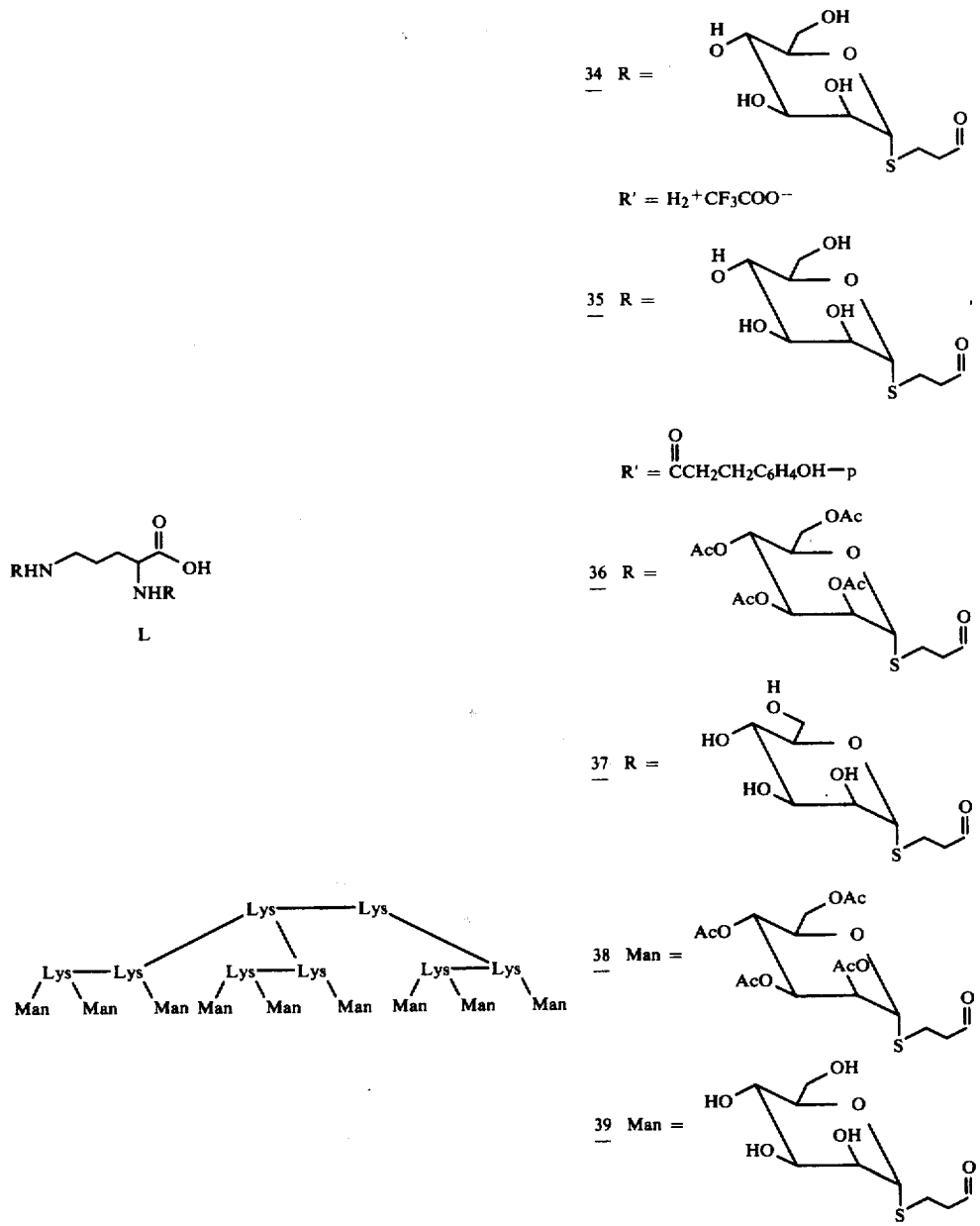

EXAMPLE 1

2-Carboxyethyl
2,3,4,6-tetra-O-acetyl-1-thio-α-D-mannopyranoside (2)

A mixture of 2-S-(2,3,4,6-tetra-O-acetyl-α-D-mannopyranosyl)-2-thiopseudourea hydrobromide (1) (90 g, 0.185 mol), freshly crystallized 3-iodopropionic acid (37 g, 0.199 mol), potassium carbonate (29.6 g, 0.215 mol), and potassium metabisulfite (37 g, 0.167 mol) in acetone (150 ml) and water (150 ml) is stirred for 45 minutes at room temperature. Hydrochloric acid (5%, 700 ml) and chloroform (700 ml) are added to the mixture. The organic layer is separated and washed with water, dried, and evaporated in vacuo to an oil (80 g, quantitative yield) that is used, without further purification, for the preparation of 3.

EXAMPLE 2 p-Nitrophenyl
3-(2,3,4,6-tetra-O-acetyl-1-thio-α-D-mannopyranosyl)-propionate (3)

p-Nitrophenol (15.3 g, 0.11 mol) is added to a solution of 2 (49 g, 0.112 mol) and DCC (23 g, 0.112 mol) in dry dichloromethane (250 ml). The mixture is stirred for 3 hours at room temperature, filtered, and the filtrate evaporated in vacuo to a residue that is purified by means of PrepPak TM 500/Silica on a Waters Associates Prep LC/System 500 at 250 ml/min using ethyl ether-dichloromethane 4:96 (v/v) as a liquid phase. Compound 3 is isolated in 55% yield (33.7 g). An analytical sample is crystallized from ethyl ether: mp 119°–121° C.; $[\alpha]_D^{27} + 76.9 \pm 1°$ (c 1.05, CHCl$_3$); MS, m/e 527 (M+-NO), 497 (M+-HOAc), 437 (M+-2HOAc), 419 [M+-OC₆H₄(pNO₂)], 331

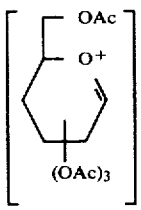

Anal. Calc. for $C_{23}H_{27}NSO_{13}$: C, 49.55; H, 4.88; N, 2.51; S, 5.75. Found: C, 49.32; H, 4.75; N, 2.84; S, 6.00.

EXAMPLE 3

N²-{N², N⁶-Bis[3-(2,3,4,6-tetra-O-acetyl-α-D-mannopyranosylthio)propionyl]-L-lysyl}-N⁶-[3-(2,3,4,6-tetra-O-acetyl-α-D-mannopyranosylthio)propionyl]-L-lysine (4)

A solution of L-lysyl-L-lysine dihydrochloride (3.47 g, 10 mmol) in trifluoroacetic acid (20 ml) is warmed to 35° C. and poured into ethyl ether (180 ml) to give L-lysyl-L-lysine trifluoroacetate salt as a precipitate that is filtered and washed with ethyl ether. A solution of this ditrifluoroacetate salt and 3 (16.71 g, 30 mmol) in DMF (90 ml) containing triethylamine (9 ml, 64 mmol) is stirred for 3 hours at room temperature, and evaporated in vacuo to a small volume. Ethyl ether is added to triturate the product, and the solvent decanted. The residue is purified by means of PrepPak TM 500/Silica on a Waters Associates Prep LC/System 500 at 250 ml/min using chloroform-methanol-water 90:10:1 (v/v/v) as a liquid phase. The title compound is isolated as a foam (12.2 g, 80%): $[α]_D^{27}+89.1±1.1°$ (c 0.95, CHCl₃).

Anal. Calc. for $C_{63}H_{92}N_4S_3O_{33}$: C, 49.47; H, 6.06; N, 3.66; S, 6.29. Found: C, 49.73; H, 6.41; N, 3.85; S, 6.16.

EXAMPLE 4

N²-{N²,N⁶-Bis-[3-(α-D-mannopyranosylthio)propionyl]-L-lysyl}-N⁶-[3-(α-D-mannopyranosylthio)propionyl]-L-lysine (5)

A solution of 4 (2.0 g) in methanol-water-triethylamine 5:4:1 (v/v/v, 20 ml) is kept overnight at room temperature, and evaporated in vacuo to a residue that is put on a column of silica gel and eluted with chloroform-methanol-water 60:40:10 (v/v/v). The desired fractions are combined and evaporated to dryness. A solution of this compound in water (15 ml) is lyophilized to give 5 (1.2 g, 90%): mp 95°–100° C.; $[α]_D^{27}+115±0.9°$ (c 1.1, H₂O); NMR (D₂O) δ: 5.37 (s, 1H, H-1), 5.34 (s, 2H, H-1), 4.36, 4.19 (q,q, α-CH), 3.24 (m, ε-CH₂), 2.95 (m, SCH₂), 2.71 (t, 2H), 2.61 (t, 4H) (SCH₂CH₂), 1.33-1.92 (CCH₂CH₂CH₂C).

Anal. Calc. for $C_{39}H_{68}N_4S_3O_{21}.0.5(CH_3CH_2)_3N$: C, 46.89; H, 7.07; N, 5.86; S, 8.94. Found: C, 46.69; H, 7.32; N, 6.13; S, 8.80.

EXAMPLE 5

N-6-t-Butyloxycarbonylaminohexyl-N²-{N²,N⁶-bis[3-(2,3,4,6-tetra-O-acetyl-α-D-mannopyranosylthio)-propionyl]-L-lysyl}-N⁶-[3-(2,3,4,6 tetra-O-acetyl-α-D-mannopyranosylthio)propionyl]-L-lysinamide (6)

6-t-Butyloxycarbonylaminohexylamine (0.648 g, 3 mmol) is added to a stirred solution of 4 (4.59 g, 3 mmol) and DCC (0.64 g, 3.1 mmol) in dichloromethane (30 ml). After 5 hours at room temperature, the mixture is filtered and the filtrate is evaporated in vacuo to a residue that is purified by means of PrepPak TM 500/Silica on a Waters Associates Prep LC/System 500 at 250 ml/min using methanol-chloroform 5:95 (v/v) as a liquid phase. Compound 6 is isolated in 63% yield (3.2 g): mp 120°–125° C. (dichloromethane-ethyl ether); $[α]_D^{27}+77.9±1.0°$ (c 1.02,CHCl₃).

Anal. Calc. for $C_{74}H_{114}N_6S_3O_{34}$: C, 51.44; H, 6.65; N, 4.86; S, 5.57. Found: C, 51.65; H, 6.64; N, 4.86; S, 5.41.

EXAMPLE 6

N-6-Aminohexyl-N²-{N²,N⁶-bis[3-(α-D-mannopyranosylthio)propionyl]-L-lysyl}-N⁶-[3-(α-D-mannopyranosylthio)propionyl]-L-lysinamide trifluoroacetate salt (7)

A solution of 6 (2.5 g, 1.45 mmol) in 90% trifluoroacetic acid (10 ml) is kept for 10 min at room temperature and evaporated in vacuo to dryness. Methanol-water-triethylamine 5:4:1 (v/v/v, 40 ml) is added and the solution is kept overnight at room temperature and evaporated to a residue (5.7 g) which contains 7 and triethylaminetrifluoroacetate. The mixture is triturated with ethyl acetate to give 7 as a solid that is filtered and dried (1.84 g, 100%): $[α]_D^{27}+83.8±1.0°$ (c 1.02, H₂O); NMR (D₂O) δ: 5.37 (s, 1H, H-1), 5.34 (s, 2H, H-1), 4.21, 4.28 (t,t,α-CH), 3.24 (m, ε-CH₂), 2.98 (m, SCH₂), 2.70 (t, 2H), 2.62 (t, 4H) (SCH₂CH₂), 1.33–1.92 (CCH₂CH₂CH₂C).

Anal. Calc. for $C_{47}H_{83}F_3N_6S_3O_{22}$: C, 45.62; H, 6.76; N, 6.79; S, 7.77; Found: C, 45.42; H, 6.83; N, 6.77; S, 7.84.

EXAMPLE 7

N-6-[3-(p-Hydroxyphenyl)propionamido]hexyl-N²-{N²,N⁶-bis[3-(α-D-mannopyranosylthio)propionyl]-L-lysyl}-N⁶-[3-(α-D-mannopyranosylthio)propionyl]-L-lysinamide (8)

Triethylamine (10 μl) is added to a solution of 7 (124 mg, 0.1 mmol) and N-succinimidyl-3-(p-hydroxyphenyl)propionate (26.5 mg, 0.1 mmol) in DMF (2 ml). The mixture is stirred for 2 hours at room temperature, and poured into ethyl ether (50 ml). The precipitate is collected and put on a column of silica gel and eluted with chloroform-methanol-water 5:5:1 (v/v/v). The desired fractions are combined and evaporated in vacuo to a residue (52 mg, containing N-hydroxysuccinimide) that is fractionated with a Sephadex G-15 column. Lyophilization of the combined desired fractions gave 8 (46 mg): $[α]_D^{27}+88°$ (c 1.0, H₂O).

Anal. Calc. for $C_{54}H_{90}N_6S_3O_{22}.2H_2O$: C, 49.60; H, 7.25; N, 6.43, S, 7.36. Found: C, 49.51; H, 7.57; N, 6.30; S, 7.52.

EXAMPLE 8

N-6-(6″-Deoxyraffinosyl)aminohexyl-N²-{N²,N⁶-bis[3-(α-D-mannopyranosylthio)propionyl]-L-lysyl}-N⁶-[3-(α-D-mannopyranosylthio)propionyl]-L-lysinamide (9)

A solution of raffinose pentahydrate (220 mg, 0.37 mmol) and 7 (229 mg, 0.185 mmol) in phosphate buffer (0.1 M, pH 7.0, 7.5 ml) is incubated with D-galactose oxidase (450 units, 60 μg) and catalase (18 mg) for 4 hours at 37° C. A solution of sodium cyanoborohydride (100 mg) in phosphate buffer (0.1 M, pH 7.0, 1.0 ml) is added, and the mixture is kept for 24 hours at room temperature. The solution is put on a column of Bio-Rad AG 1-X8(HCO$_3^-$) ion exchange resin and eluted with water. The desired fractions are combined and lyophilized to give a fluffy material (400 mg) that is fractionated by a Sephadex G-15 column (v$_o$=60 ml, flow rate 0.15 ml/min). Fractions 30 and 31 (2.5 ml/fraction) are lyophilized to give 9 (58 mg, 20%): [α]$_D^{27}$+100.8° (c 0.83, H$_2$O); NMR (D$_2$O) δ: 5.47 (d, J$_{1,2}$=4.0 Hz, GlcH-1), 5.07 (d, J$_{1,2}$=3.5 Hz, Gal H-1), 5.38 (s, 1H, ManH-1), 5.36 (s, 2H, ManH-1), 3.24 (m, ε-CH$_2$), 2.95 (m,CH$_2$), 2.72 (t, 2H), 2.63 (t, 4H) (SCH$_2$CH$_2$), 1.28–1.90 (CCH$_2$CH$_2$CH$_2$C).

Anal. Calc. for C$_{63}$H$_{112}$N$_6$S$_3$O$_{35}$.H$_2$O: C, 46.49; H, 7.06; N, 5.16. Found: 46.36; H, 7.27; N, 5.16.

EXAMPLE 9

21-Dexamethasone(p-nitrophenyl)carbonate p-Nitrophenylchloroformate (2.3 g, 11.4 mmol) is added to a stirred solution of dexamethasone (3.92 g, 10 mmol) in chloroform (100 ml) containing pyridine (10 ml). The resulting solution is kept overnight at room temperature, and washed successively with water, dilute hydrochloric acid, and water. The solution is dried and evaporated in vacuo to a residue that is triturated with ethyl ether to give crystals (5.5 g, 100%). An analytical sample is recrystallized from dichloromethane-ethyl ether: mp 204°–205° C.; [α]$_D^{27}$+114±0.9° (c 1.1, CHCl$_3$); NMR (CDCl$_3$) δ: 8.33 (d, J=9.0 Hz), 7.45 (d, J=9.0 Hz, aromatic), 7.19 (d, J$_{1,2}$=10.0 Hz, H-1), 6.36 (d,d, J$_{2,4}$=1.5 Hz, H-2), 6.13 (d, H-4), 5.04, 5.14 (d,d,J$_{AB}$=18.0 Hz, CH$_2$-21), 4.37 (m, J$_{H,F}$=9.0 Hz, H-11), 1.53 (s, CH$_3$-19), 1.06 (s, CH$_3$-18), 0.95 (d,J=7.0 Hz, 16α-CH$_3$).

Anal. Calc. for C$_{29}$H$_{32}$FNO$_9$: C, 62.47; H, 5.79; F, 3.41; N, 2.51. Found: C, 62.21; H, 5.89; F, 3.32; N, 2.42.

EXAMPLE 10

N-α-{N$^α$,N$^ε$-Bis[3-(α-D-mannopyranosylthio)propionyl]-L-lysyl}-N-[6-(carboxyamino)hexyl]-N$^ε$-[3-(α-D-mannopyranosylthio)propionyl]-L-lysinamide, 21-ester with dexamethasone (10)

Triethylamine (0.3 ml) is added to a solution of 7 (210 mg, 0.17 mmol) and 21-dexamethasone (p-nitrophenyl)-carbonate (140 mg, 0.25 mmol) in DMF (2 ml). The solution is kept overnight at room temperature and poured with stirring into ethyl ether. The solid (340 mg) is collected and put on a column of silica gel and eluted with chloroform methanol-water 60:40:4 (v/v/v). Compound 10 is isolated in 69% yield (170 mg). An analytical sample is recrystallized from methanol-ethyl ether: mp 219°–220° C.; [α]$_D^{27}$+102° (c 1.0, H$_2$O); NMR (CD$_3$OD) δ: 7.47 (d, J$_{1,2}$=10.0 Hz, H-1), 6.32 (d,d, J$_{2,4}$=1.5 Hz, H-2), 6.11 (d, H-4), 5.33 (s, 1H, ManH-1), 5.30 (s, 2H, ManH-1), 4.28 (m, H-11), 1.60 (s, CH$_3$-19), 1.34–1.58 (m, CCH$_2$CH$_2$CH$_2$C), 1.01 (s, CH$_3$-18), 0.86 (d, J=7.0 Hz, 16α-CH$_3$).

Anal. Calc. for C$_{68}$H$_{109}$FN$_6$S$_3$O$_{26}$.CH$_3$OH: C, 52.66; H, 7.24; F, 1.21; N, 5.34; S, 6.11. Found: C, 52.42; H, 7.40; F, 1.19; N, 5.17; S, 6.26.

EXAMPLE 10A

N$^2$-{N$^2$,N$^6$-Bis[3-(α-D-mannopyranosylthio)propionyl]-L-lysyl}-N$^6$-[3-(α-D-mannopyranosylthio)propionyl]-L-lysine, 21-ester with dexamethasone (10A)

Dexamethasone-21-methanesulfonate (69 mg, 0.15 mmol) is added under N$_2$ to a stirred suspension of the potassium salt of 5 [prepared by adding KOH (0.2 N, 0.72 ml) to 5 (154 mg) and lyophilized] in DMF (3 ml) and the mixture is heated overnight at 50° C. The reaction mixture is evaporated in vacuo to a residue that is put on a column of silica gel and eluted with CHCl$_3$-MeOH-H$_2$O 60:40:4 (v/v/v). The desired fractions are combined and evaporated to give the title compound (42 mg, 21%), R$_f$ 0.7.

EXAMPLE 11

N$^2$N$^6$-Bis[3-(2,3,4,6-tetra-O-acetyl-α-D-mannopyranosylthio)propionyl]-L-lysine (11)

Triethylamine (417 μl, 3 mmol) is added to a solution of 3 (1.12 g, 2 mmol) and L-lysine trifluoroacetate salt (0.26 g, 1 mmol) in DMF (10 ml). The mixture is stirred for 18 hours at room temperature and evaporated in vacuo to a residue that is put on a column of silica gel and eluted with chloroform-methanol-water 90:10:1 (v/v/v). The title compound is isolated in 69% yield (0.68 g): [α]$_D^{27}$+95.3±1.0° (c 1.0, CHCl$_3$).

Anal. Calc. for C$_{40}$H$_{58}$N$_2$S$_2$O$_{22}$.H$_2$O: C, 47.99; H, 6.04; N, 2.80; S, 6.41. Found: C, 47.92; H, 5.96; N, 2.75; S, 6.25.

EXAMPLE 12

N$^2$,N$^6$-Bis[3-(2,3,4,6-tetra-O-acetyl-α-D-mannopyranosylthio)propionyl]-D-lysine (13)

Compound 13 is prepared as for 11, and has [α]$_D^{27}$+72.6±1.0° (c 1.0, CHCl$_3$).

Anal. Calc. for C$_{40}$H$_{58}$N$_2$S$_2$O$_{22}$.H$_2$O: C, 47.99; H, 6.04; N, 2.80; S, 6.41. Found: C, 48.34; H, 5.91; N, 2.74; S, 6.26.

EXAMPLE 13

N$^2$,N$^6$-Bis[3-(α-D-mannopyranosylthio)propionyl]-L-lysine (12)

A solution of 11 (280 mg. 0.28 mmol) in methanol-water-triethylamine 5:4:1 (v/v/v, 7 ml) is kept for 3 hours at room temperature, and evaporated in vacuo to dryness. The residue is put on a Sephadex G-15 column and eluted with water. The desired fractions are combined and lyophilized to give 12 (140 mg, 77%): [α]$_D^{27}$+115° (c 1.0, H$_2$O); NMR (D$_2$O) δ: 5.34, 5.36 (s,s, H-1), 4.2 (q, α-CH), 3.22 (m, ε-CH$_2$), 2.94 (m, SCH$_2$), 2.67 (t), 2.60 (t) (SCH$_2$CH$_2$), 1.83, 1.71 (m,m β-CH$_2$), 1.56 (m,δ-CH$_2$), 1.42 (m, γ-CH$_2$).

Anal. Calc. for C$_{24}$H$_{42}$N$_2$S$_2$O$_{14}$.0.5(CH$_3$CH$_2$)$_3$N: C, 46.51; H, 7.16; N, 5.02; S, 9.20. Found: C, 46.48; H, 7.10; N, 4.96; S, 9.33.

EXAMPLE 14

N$^2$,N$^6$-Bis[3-(α-D-mannopyranosylthio)propionyl]-D-lysine (14)

This compound is prepared similarly to 12, and has identical NMR spectrum as 12: [α]$_D^{27}$+133.3° (c 1.0, H$_2$O).

Anal. Calc. for C$_{24}$H$_{42}$N$_2$S$_2$O$_{14}$0.5(CH$_3$CH$_2$)N, 2H$_2$O: C, 44.22; H, 7.35; N, 4.77. Found: C, 44.55; H, 7.52; N, 5.06.

EXAMPLE 15

N²-{N²-{N²,N⁶-Bis[3-(2,3,4,6-tetra-O-acetyl-α-D-mannopyranosylthio)propionyl]-L-lysyl}-N⁶-[3-(2,3,4,6-tetra-O-acetyl-α-D-mannopyranosylthio)propionyl]-L-lysyl}-N⁶-[3-(2,3,4,6-tetra-O-acetyl-α-D-mannopyranosylthio)propionyl]-L-lysine (15)

A mixture of L-lysyl-L-lysyl-L-lysine tetracetate salt (0.321 g. 0.5 mmol), and 3 (1.11 g, 2 mmol) in DMF (10 ml) containing triethylamine (348 μl, 2.5 mmol) is stirred overnight at room temperature, and evaporated in vacuo to dryness. The residue is put on a column of silica gel and eluted with chloroform-methanol 95:5 (v/v). The title compound is isolated as a crystalline material (0.135 g, 13%): mp 120°–121° C. (MeOH-Et₂O); $[\alpha]_D^{27} + 86.7 \pm 1.0°$ (c 1.0, CHCl₃).

Anal. Calc. for $C_{86}H_{126}N_6S_4O_{44}.3H_2O$: C, 48.49; H, 6.25; N, 3.95; S, 6.02. Found: C, 48.40; H, 6.24; N, 4.16; S, 5.85.

EXAMPLE 16

N²-{N²-{N²,N⁶-Bis[3-(α-D-mannopyranosylthio)propionyl]-L-lysyl}-N⁶-[3-(α-D-mannopyranosylthio)propionyl]-L-lysyl}-N⁶-[3-(α-D-mannopyranosylthio)propionyl]-L-lysine (16)

A solution of 15 (52 mg, 0.025 mmol) in methanol-water-triethylamine 5:4:1 (v/v/v, 1 ml) is kept for 3 hours at room temperature, and evaporated in vacuo to a residue that is put on a Sephadex G-15 column and eluted with water. Fractions 1–4 (12 ml), eluted after blue dextran, are collected and lyophilized to give 16 (25.1 mg, 71%): $[\alpha]_D^{27} + 96.2°$ (c 1.0, H₂O); NMR (D₂O)δ: 5.37 (s, 1H, H-1), 5.34 (s, 3H, H-1) 4.34 (2H), 4.18 (1H) (α-CH), 3.22 (m, ε-CH₂), 2.93 (m, SCH₂), 2.70 (t, 2H), 2.60 (t, 6H) (SCH₂CH₂), 1.34–1.94 (CCH₂CH₂CH₂C).

Anal. Calc. for $C_{54}H_{94}N_6S_4O_{28}$: C, 46.21; H, 6.75; N, 5.99. Found: C, 46.17; H, 6.99; N, 6.17.

EXAMPLE 17

N²-{N²,N⁶-Bis[1-imino-2-(α-D-mannopyranosylthio)ethyl]-L-lysyl}-N⁶-[1-imino-2-(α-D-mannopyranosylthio)ethyl]-L-lysine (17)

Cyanomethyl 2,3,4,6-tetra-O-acetyl-1-thio-α-D-mannopyranoside (2.02 g, 5 mmol) is treated with sodium methoxide (0.2 N) in methanol (50 ml) for 20 hours at room temperature, and the solution is evaporated in vacuo to a foam. A solution of L-lysyl-L-lysine dihydrochloride (150 mg, 0.43 mmol) in sodium borate (2.5 M, pH 10, 10 ml) is added, and the resulting solution is kept for 4 hours at room temperature. The mixture is fractionated with a Sephadex G-25 column (1.5×100 cm) and fractions containing 17 are lyophilized (105 mg, 25%): $[\alpha]_D^{27} + 124°$ (c 0.75, H₂O); NMR (D₂O)δ: 5.34, (s, 2H, H-1), 5.33 (s, 1H, H-1), 4.19 (t, J=6.5 Hz, α-CH), 3.33 (t, J=6.5 Hz, ε-CH₂), 1.41–1.94 (m,CCH₂CH₂CH₂C).

Anal. Calc. for $C_{36}H_{65}N_7S_3O_{18}.2H_2O$: C, 42.55; H, 7.04; N, 9.64; S, 9.46. Found: C, 42.61; H, 7.19; N, 10.07; S, 9.25.

EXAMPLE 18 p-Nitrophenyl 3-(2,3,4,6-tetra-O-acetyl-1-thio-β-D-galactopyranosyl)-propionate (18)

2-Carboxyethyl 2,3,4,6-tetra-O-acetyl-1-thio-β-D-galactopyranoside

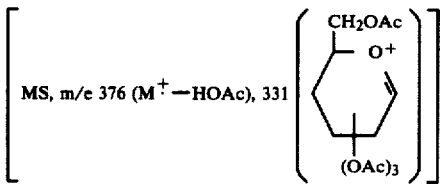

is prepared in a similar manner as for 2. p-Nitrophenol (7.7 g, 55 mmol) is added to a solution of the above compound (24 g, 55 mmol) and DCC (12 g, 58 mmol) in dichloromethane (100 mL), and the mixture is stirred for 1 hour at room temperature, filtered, and the filtrate is evaporated to dryness. The residue is purified by means of PrepPak ™ 500/Silica on a Waters Associates Prep LC/System 500 at 250 ml/min using ethyl ether-dichloromethane 4:96 (v/v) as a liquid phase. The title compound is isolated in 54% yield (16.6 g): mp 94°–96° C. (CH₂Cl₂-(et₂O); $[\alpha]_D^{27} - 18.3 \pm 1.0$ (c 1.0, CHCl₃); MS, m/e 527 (M†-NÖ), 497 (M†-HOAc), 437 (M†-2HOAc), 419 (M†-OC₆H₄NO₂-p),

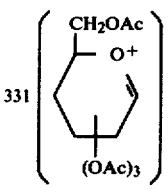

Anal. Calc. for $C_{23}H_{27}NSO_{13}$: C, 49.55; H, 4.88; N, 2.51; S, 5.75. Found: C, 49.52; H, 4.99; N, 2.45; S, 5.83.

EXAMPLE 19

N²-{N²,N⁶-Bis[3-(2,3,4,6-tetra-O-acetyl-β-D-galactopyranosylthio)propionyl]-L-lysyl}-N⁶-[3-(2,3,4,6-tetra-O-acetyl-β-D-galactopyranosyl)propionyl]-L-lysine (19)

A solution of L-lysyl-L-lysine ditrifluoroacetate salt (2.2 g, 4.4 mmol) and 18 (7.41 g, 13.2 mmol) in DMF (50 ml) containing triethylamine (2.5 ml) is stirred overnight at room temperature, and evaporated in vacuo to dryness. The residue is purified by means of Prep-Pak ™ 500/Silica on a Waters Associates Prep LC/System 500 at 250 ml/min using chloroform-methanol-water 90:10:0.5 (v/v/v) as a liquid phase. Compound 19 is isolated in 80% yield (5.35 g): $[\alpha]_D^{27} 0 \pm 0.8°$ (c 1.2, CHCl₃).

Anal. Calc. for $C_{63}H_{92}N_4S_3O_{33}$: C, 49.47; H, 6.06; N, 3.66; S, 6.29. Found: C, 49.43; H, 6.18; N, 3.78; S, 6.12.

EXAMPLE 20

N²-{N²,N⁶-Bis[3-(β-D-galactopyranosylthio)propionyl]-L-lysyl}-N⁶-[3-(β-D-galactopyranosylthio)propionyl]-L-lysine (20)

A solution of 19 (50 mg) in methanol-water-triethylamine 5:4:1 (v/v/v, 2 ml) was kept for 18 hours at room temperature, and evaporated in vacuo to dryness. The residue was put on a column of silica gel and eluted with chloroform-methanol-water 60:40:10 (v/v/v). The title compound was isolated in 61% yield (20 mg): $R_F$ 0.15 (CHCl₃-MeOH-H₂O, 60:40:10); NMR (D₂O)δ: 4.51 (d, $J_{1,2}$=9.5 Hz, 2H, H-1), 4.52 (d, $J_{1,2}$=9.5 Hz, 1H, H-1), 4.34, 4.18 (q, q, α-CH), 3.99 (d, $J_{4,3}$=3.0 Hz, 3H, H-4), 3.22 (m, εCH₂), 3.02 (m, SCH₂), 2.70 (t, J=6.5 Hz, 2H, SCH₂CH₂), 2.62 (t, J=6.5 Hz, 4H, SCH₂CH₂); $[\alpha]_D^{27}$ −17.3° (c 1.5, H₂O).

EXAMPLE 21

N-6-t-Butyloxycarbonylaminohexyl-N²-{N²,N⁶-bis[3-(2,3,4,6-tetra-O-acetyl-β-D-galactopyranosylthio)propionyl]-L-lysyl}-N⁶-[3-(2,3,4,6-tetra-O-acetyl-β-D-galactopyranosylthio)propionyl]-L-lysinamide (21)

6-t-Butyloxycarbonylaminohexylamine (0.432 g, 2 mmol) is added to a stirred solution of 19 (3.06 g, 2 mmol) and DCC (0.45 g, 2.2 mmol) in dichloromethane (30 ml). After 5 hours at room temperature, the mixture is processed in the same manner as for 6. The title compound is isolated in 66% yield (2.26 g): mP 50° C. (softened, CH₂Cl₂-et₂O); $[\alpha]_D^{27}$ −4.1±0.9° (c 1.05, CHCl₃).

Anal. Calc. for C₇₄H₁₁₄N₆S₃O₃₄: C, 51.44; H, 6.65; N, 4.86; S, 5.57. Found: C, 51.53; H, 6.74; N, 4.61; S, 5.47.

EXAMPLE 22

N-6-Aminohexyl-N²-{N²,N⁶-bis[3-(β-D-galactopyranosylthio)propionyl]-L-lysyl}-N⁶-[3-(β-D-galactopyranosylthio)propionyl]-L-lysinamide trifluoroacetate salt (22)

A solution of 21 (1.2 g, 0.69 mmol) in 90% trifluoroacetic acid (2 ml) is kept for 10 minutes at room temperature and evaporated in vacuo to dryness. Methanol-water-triethylamine 5:4:1 (v/v/v, 20 ml) is added, and the solution is kept overnight at room temperature and evaporated to a residue that is put on a column of silica gel and eluted with chloroform-methanol-water 2:2:1 (v/v/v) followed by methanol-ammonium hydroxide 1:1 (v/v) Fractions containing 22 are combined and evaporated to dryness. Methanol is added, filtered, and the filtrate is evaporated in vacuo to give 22 (0.33 g, 42%): $[\alpha]_D^{27}$ −8.4±1.2° (c 0.8, H₂O); NMR (D₂O)δ: 4.52 (d, $J_{1,2}$=10.0 Hz, 1H, H-1), 4.50 (d, $J_{1,2}$=10.0 Hz, 2H, H-1), 4.25 (m, α-CH), 3.99 (d, $J_{4,3}$=2.5 HZ, H-4), 3.22 (m, ε-CH₂), 3.01 (m, SCH₂), 2.72 (t, 2H), 2.62 (t, 4H) (SCH₂CH₂), 1.32–1.88 (CCH₂CH₂CH₂C).

EXAMPLE 23

2-Carboxyethyl 2,3,4-tri-O-acetyl-1-thio-β-L-fucopyranoside (23)

A solution of 2,3,4-tri-O-acetyl-1-thio-β-L-fucopyranose (1.49 g, 4.87 mmol) and freshly crystallized 3-iodopropionic acid (0.97 g, 4.86 mmol) in dichloromethane (20 ml) containing triethylamine (1.35 ml) is kept for 16 hours at room temperature. Hydrochloric acid (2.5 N, 20 ml) and dichloromethane (10 ml) are added and the solution is washed with water, dried, and evaporated in vacuo to a residue that is put on a column of silica gel and eluted with chloroform-methanol-water, 92.5:7.5:0.75 (v/v/v). Compound 23 is isolated in 87% yield (1.6 g), and used, without further purification, for the preparation of 24.

EXAMPLE 24 p-nitrophenyl 3-(2,3,4-tri-O-acetyl-1-thio-β-L-fucopyranosyl)propionate (24)

p-Nitrophenol (2.6 g. 18.7 mmol) is added to a solution of 23 (7.0 g, 18.5 mmol) and DCC (3.8 g, 18.5 mmol) in dichloromethane (20 ml), and the mixture is stirred for 3 hours at room temperature and diluted with ethyl ether (50 ml). The resulting mixture is poured through a sintered funnel packed with silica gel, and the filtrate is evaporated in vacuo to dryness. The residue is purified by means of PrePak ™ 500/Silica on a Waters Associates Prep LC/System 500 at 250 ml/min using ethyl ether-dichloromethane 4:96 (v/v) as a liquid phase. Compound 24 is isolated in 38% yield (3.5 g). An analytical sample is crystallized from ethyl ether: mp 96°–97° C.; $[\alpha]_D^{27}$ +29.9±0.5° (c, 1.06, CHCl₃); MS, m/e 469 (M+-NO), 439 (M+-HOAc), 379 (M+-2HOAc), 361 (M+-OC₆H₄NO₂(p)],

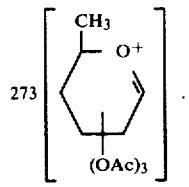

Anal. Calc. for C₂₁H₂₅NSO₁₁: C, 50.49; H, 5.05; N, 2.80; S, 6.42. Found: C, 50.33, H, 5.09; N, 2.77; S, 6.41.

EXAMPLE 25

N²-{N²,N⁶-Bis[3-(2,3,4—tri-O-acetyl-β-L-fucopyranosylthio)propionyl]-L-lysyl}-N⁶[3-(2,3,4-tri-O-acetyl-β-L-fucopyranosylthio)propionyl]-L-lysine (25)

A solution of L-lysyl-L-lysine ditrifluoroacetate salt (0.6 g, 1.32 mmol) and 24 (2.0 g, 4 mmol) in DMF (10 ml) containing triethylamine (900 μl, 6.5 mmol) is stirred overnight at room temperature. The reaction mixture is worked up in the same manner as for 4 to give the title compound (1.55 g, 87%): $[\alpha]_D^{27}$ +12.3±1.2° (c 0.83, CHCl₃).

Anal. Calc. for C₅₇H₈₆N₄S₃O₂₇0.5 (CH₃CH₂)₃N: C, 51.25; H, 6.70; N, 4.48; S, 6.84. Found: C, 51.00; H, 6.53; N, 4.67; S, 6.73.

EXAMPLE 26

N²-{N²,N⁶-Bis[3-(β-L-fucopyranosylthio)propionyl]-L-lysyl}-N⁶[3-(β-L-fucopyranosylthio)propionyl]-L-lysine (26)

A solution of 25 (500 mg) in methanol-water-triethylamine 5:4:1 (v/v/v, 5 ml) is kept for 3 hours at room temperature and worked-up in the same manner as for 5 to give the title compound (300 mg, 83%): $[\alpha]_D^{27}$ +28.4±0.9° (c 1.0 H₂O); NMR (D₂O)δ: 4.48 (d, $J_{1,2}$=9.5 Hz, 1H, H-1), 4.46 (d, $J_{1,2}$=9.5 Hz, 2H, H-1), 4.17, 4.32 (q,q, α-CH), 3.22 (m, ε-CH₂), 2.98 (m, SCH₂), 2.69 (t, 1H), 2.61 (t, 2H) (SCH₂CH₂), 1.34–1.90 (m, C-CH₂CH₂CH₂C), 1.25 (d, J=6.0 Hz, CH₃-6).

Anal. Calc. for $C_{39}H_{68}N_4S_3O_{18}0.5(CH_3CH_2)_3N.1.5\text{-}H_2O$: C, 47.83; H, 7.50; N, 5.98; S, 9.12. Found: C, 47.86; H, 7.44; N, 5.88; S, 9.27.

EXAMPLE 27

6-Phthalimido-1-(5-cholesten-3β-yloxy)hexane

A mixture of 6-(5-cholesten-3β-yloxy)hexyl iodide (1.0 g) and potassium phthalimide (1.0 g) in DMF (25 ml) is heated with stirring for 0.5 hours at 85°–90° C. (bath temperature). The mixture is filtered and the filtrate is evaporated in vacuo to a residue that is partitioned between chloroform and water. The organic layer is washed with aqueous sodium thiosulfate and water, dried, and evaporated to a syrup that crystallizes upon standing. Recrystallization from petroleum ether gives the title compound (0.92 g, 89%) mp 80° C.

Anal. Calc. for $C_{41}H_{61}NO_3$: C, 79.95; H, 9.98; N, 2.27. Found: C, 79.73; H, 10.30; N, 2.42.

EXAMPLE 28

6-(5-Cholesten-3β-yloxy)hexylamine

A solution of 6-phthalimido-1-(5-cholesten-3β-yloxy)hexane (500 mg) and n-butylamine (5 ml) in methanol (10 ml) and chloroform (5 ml) is heated under reflux for 1 hour. The solution is evaporated in vacuo to a residue that is put on a column of silica gel and eluted with CHCl$_3$-MeOH-NH$_4$OH 90:10:1 (v/v/v). The ninhydrin positive fractions are combined and evaporated to give the title compound (170 mg, 43%).

Anal. Calc. for $C_{33}H_{59}NO.HCl$: C, 75.89; H, 11.58; N, 2.68; Cl, 6.79. Found: C, 76.42; H, 11.75; N, 2.50; Cl, 6.90.

EXAMPLE 29

N-6-(5-Cholesten-3β-yloxy)hexyl-N$^2${N$^2$,N$^6$-bis[(2,3,4,6-tetra-O-acetyl-α-D-mannopyranosylthio)-propionyl]-L-lysyl}-N$^6$-[(2,3,4,6-tetra-O-acetyl-α-D-mannopyranosylthio)propionyl-L-lysinamide (27)

6-(5-Cholesten-3β-yloxy)hexylamine (100 mg, 0.21 mmol) is added to a stirred solution of 4 (315 mg, 0.21 mmol) and DCC (43 mg, 0.21 mmol) in dichloromethane (5 ml). After 2 hours at room temperature, the mixture is filtered and the filtrate is evaporated in vacuo to a residue that is put on a column of silica gel and eluted with CHCl$_3$-MeOH 98:2 followed by CHCl$_3$-MeOH 96:4 (v/v). The desired fractions are combined and evaporated to a syrup (428 mg) that is triturated with anhydrous ethyl ether. The solid is filtered and washed with ethyl ether to give the title compound (306 mg, 74%): mp 154°–164° C.; $[\alpha]_D^{27} + 61.3°$ (c 1.0, CHCl$_3$).

Anal. Calc. for $C_{96}H_{149}N_5S_3O_{33}$: C, 57.73; H, 7.52; N, 3.51; S, 4.82. Found: C, 57.57; H, 7.64; N, 3.44; S, 5.10.

EXAMPLE 30

N-6-(5-Cholesten-3β-yloxy)hexyl-N$^2$-{N$^2$,N$^6$-bis[3-(α-D-mannopyanosylthio)propionyl-L-lysyl}N$^6$-[3-(α-D-mannopyranosylthio)propionyl-L-lysinamide (28)

A solution of 27 (200 mg) in methanol-water-triethylamine 5:4:1 (v/v/v, 5 ml) is kept for 2 hours at room temperature, and evaporated in vacuo to dryness. The residue is put on a column of silica gel and eluted with CHCl$_3$-MeOH-H$_2$O 70:30:3 (v/v/v). The desired fractions are combined and evaporated to a syrup that is triturated with ethyl ether-petroleum ether to give a glass (112 mg, 75%): $[\alpha]_D^{27} + 71.2°$ (c 1.25, DMF).

Anal. Calc. for $C_{72}H_{125}N_5S_3O_{21}H_2O$: C, 57.23; H, 8.47; N, 4.64; S, 6.37. Found: C, 57.13; H, 8.40; N, 4.35; S, 6.26.

EXAMPLE 31

Carboxylmethyl 2,3,4,6-tetera-O-acetyl-1-thio-α-D-mannopyranoside (29)

A mixture of 1 (2.45 g, 5 mmol), iodoacetic acid (0.93 g, 5 mmol), potassium carbonate (0.8 g) and potassium metabisulfite (1.0 g) in acetone (10 ml) and water (10 ml) is stirred for 45 min at room temperature. Hydrochloric acid (5%, 40 ml) and chloroform (40 ml) are added to the mixture. The organic layer is separated, washed with water, dried, and evaporated in vacuo to give 29 (1.7 g, 41%): $[\alpha]_D^{27} + 113 \pm 0.8°$ (c 1.2, CHCl$_3$); MS, m/e 423 (M+ +1) 405 (M+-OH), 363 (M+ +1-HOAc),

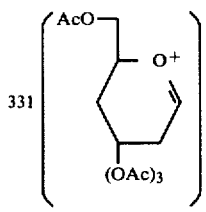

331

Anal. Calc. for $C_{16}H_{22}SO_{11}$: C, 45.49; H, 5.25; S, 7.59. Found: C, 45.15; H, 5.34; S, 7.46.

EXAMPLE 32 p-Nitrophenyl (2,3,4,6-tetra-O-ocetyl-1-thio-α-D-mannopyranosyl)acetate (30)

p-Nitrophenol (0.33 g, 2.37 mmol) is added to a solution of 29 (1.0 g, 2.8 mmol) in dry dichloromethane (10 ml). The mixture is stirred for 3 hours at room temperature, filtered, and the filtrate is evaporated in vacuo to a residue (1.4 g) which is used, without further purification, for the preparation of 31.

EXAMPLE 33

N$^2$-{N$^2$,N$^6$-Bis[(2,3,4,6-tetra-O-acetyl-α-mannopyranosylthio)acetyl-L-lysyl}-N$^6$-[(2,3,4,6-tetera-O-acetyl-α-D-mannopyranosylthio)acetyl]-L-lysine (31)

A solution of L-lysyl-L-lysine trifluoroacetate salt, prepared from L-lysyl-L-lysine dihydrochloride (0.23 g, 0.66 mmol) and trifluoroacetic acid, and 30 (1.09 g, 2 mmol) is DMF (10 ml) containing triethylamine (400 μl) is stirred overnight at room temperature. The mixture is evaporated in vacuo to a residue that is put on a column of silica gel and eluted with chloroform-methanol-water 90:10:1 (v/v/v). The desired fractions are combined and evaporated to give 31 (0.73 g, 80%): $[\alpha]_D^{27} + 123 \pm 2.0°$ (c 1.28, CHCl$_3$).

Anal. Calc. for $C_{60}H_{84}N_4S_3O_{33}2H_2O$: C, 47.36; H, 5.83; N, 3.68. Found: C, 47.59; H, 5.87; N, 3.70.

EXAMPLE 34

N$^2$-{N$^2$,N$^6$-Bis[(α-D-mannopyranosylthio)acetyl]-L-lysyl}-N$^6$-[(α-D-mannopyranosylthio)acetyl]-L-lysine (32)

A solution of 31 (50 mg) in methanol-water-triethylamine 5:4:1 (v/v/v), 1 ml) is kept overnight at room temperature, and evaporated in vacuo to a residue that is put on a column of silica gel and eluted with chloroform-methanol-water 60:40:10 (v/v/v). The title compound is isolated as a foam (10 mg), $R_f$ 0.15.

EXAMPLE 35

N-6-t-Butyloxycarbonylaminohexyl-$N^2,N^6$-bis[3-(2,3,4,6-tetra-O-acetyl-α-D-mannopyranosylthio)propionyl]-L-lysinamide (33)

6-t-Butyloxycarbonylaminohexylamine (275 mg, 1.1 mmol) is added to a stirred solution of 11 (983 mg, 1 mmol) and DCC (220 mg, 1.07 mmol) in dichloromethane (10 ml). The mixture is stirred for 5 hours at room temperature, filtered, and the filtrate is evaporated in vacuo to dryness. The residue is put on a column of silica gel and eluted with (CHl$_3$-MeOH-H$_2$O 95:5:5 (v/v/v) to give the title compound (1.07 g, 97%) which is triturated with Et$_2$O: mp 68°–71° C. (sintered); $[\alpha]_D^{27}+68.1\pm1.1°$ (c 1.0, CHCl$_3$).

Anal. Calc. for $C_{51}H_{80}N_4S_2O_{23}$: C, 51.85; H, 6.83; N, 4.74; S, 5.43. Found: C, 51.66; H, 6.99; N, 4.66; S, 5.22.

EXAMPLE 36

N-6-Aminohexyl-$N^2,N^6$-bis[3-(α-D-mannopyranosylthio)propionyl]-L-lysinamide trifluoroacetate salt (34)

A solution of compound 33 (510 mg, 0.43 mmol) in dichloromethane (3 ml) and trifluoroacetic acid (1 ml) is kept for 2 hours at room temperature and evaporated in vacuo to dryness. Methanol-water-triethylamine 5:4:1 (v/v/v, 5 ml) is added and the solution is kept at room temperature for 3 hours and evaporated to a residue which is purified by a Sephadex G-25 column to give the title compound (370 mg, 100%): NMR (D$_2$O)δ: 5.38 (d, $J_{1,2}=1.5$ Hz), 5.36 (d, $J_{1,2}=1.5$ Hz) (H-1), 4.23 (t, α-CH) 2.98 (m, SCH$_2$), 2.70 (t), 2.63 (t) (SCH$_2$CH$_2$), 1.34–1.88 (CCH$_2$CH$_2$CH$_2$C).

EXAMPLE 37

N-6-[3-(p-Hydroxyphenyl)propionamido]hexyl-$N^2,N^6$-bis[3-(α-D-mannopyranosylthio)propionyl]-L-lysinamide (35)

Treiethylamine (35 μl) is added to a solution of 34 (180 mg, 0.24 mmol) and N-succinimidyl-3-(p-hydroxyphenyl)propionate (65 mg, 0.25 mmol) in water (0.5 ml) and DMF (0.5 ml). The mixture is stirred for 10 min and evaporated in vacuo to a residue which is put on a column of silica gel and eluted with CHCL$_3$-MeOH-H$_2$O 70:30:3 (v/v/v). The desired fractions are combined and evaporated to give the title compound (80 mg, 38%), $R_f$ 0.25.

EXAMPLE 38

$N^2,N^5$-Bis[3-(2,3,4,6-tetra-O-acetyl-α-D-mannopyranosylthio)propionyl]-L-ornithine (36)

A solution of L-ornithine hydrochloride (169 mg, 1 mmol) and 3 (1.12 g, 2 mmol) in DMF (20 ml) containing triethylamine (4.7 μl, 3 mmol) is stirred for 48 hours at room temperature. The reaction mixture is evaporated in vacuo to a residue which is partitioned between chloroform and water. The organic layer is dried and evaporated to a small volume that is put on a column of silica gel and eluted with CHCl$_3$-MeOH-H$_2$O 90:10:1 (v/v/v). The desired fractions are combined, evaporated, and triturated with et$_2$O to give the title compound (250 mg, 26%).

EXAMPLE 39

$N^2,N^5$-Bis[3-(α-D-mannopyranosylthio)propionyl]-L-ornithine (37)

A solution of 36 (100 mg) in MeOH-H$_2$O-Et$_3$N 5:4:1 (v/v/v, 3 ml) is kept for 3 hours at room temperature, and evaporated to a residue which is put on a Sephadex G-25 column and eluted with water. The desired fractions are combined and lyophilized to give the title compound (65 mg, 100%): NMR (D$_2$O)δ: 5.38 (d, $J_{1,2}=1.5$ Hz), 5.35 (d,$J_{1,2}=1.5$ Hz) (H-1), 2.70 (t), 2.63 (t) (SCH$_2$CH$_2$).

EXAMPLE 40

Per O-acetyl-Man$^9$Lys$^8$ (38)

p-Nitrophenol (420 mg, 3.03 mmol) is added to a solution of 4 (4.59 g, 3 mmol) and DCC (630 mg, 3.06 mmol) in dichloromethane (20 ml) and the mixture is stirred for 3 hours at room temperature. The reaction mixture is filtered and the filtrate is evaporated in vacuo to a residue which is taken up in DMF (10 ml) and added to a solution of L-lysyl-L-lysine trifluoroacetate salt (500 mg, 1 mmol) in DMF (40 ml) containing triethylamine (2.82 ml). The mixture is stirred for 16 hours at room temperature, filtered, and the filtrate is evaporated to a residue which is triturated with et$_2$O to give a solid which is purified by silica gel column chromatography with CHCl$_3$-MeOH-H$_2$O 90:10:1 (v/v/v) as eluent.

EXAMPLE 41

Man$^9$-Lys$^8$ (39)

The product of the preceeding example was treated as described in the procedure of Example 34 to obtain the title product.

EXAMPLE 42

Man$^3$Lys$^2$-Glucocerebrosidase Conjugate (42)

A solution of β-glucocerebrosidase (3.7 mg, 1 ml; $3.7\times10^6$ units of enzymic activity) in 60% ethylene glycol in 100 mM citrate phosphate buffer, pH 5.0/5 mM EDTA/1 mM dithiothreitol is dialyzed agains 20% ethylene glycol in phosphate buffer (pH 5.7, 100 ml; 4 changes in 24 hours). 1-Ethyl-3-(3-dimethylaminopropyl)carbodiimide hydrochloride (ECD) (1 mg) and 5 (2 mg) are added to the above dialyzed β-glucocerebrosidase, and the mixture is stirred under nitrogen for 26 hours at 4° C. and put on a Sephadex G-25 column (46 cm × 1 cm, 36 ml), previously equilibrated with 20% ethylene glycol in citrate phosphate buffer, pH 5.0/5 mM EDTA/1 mM dithiothreitol. The conjugate is eluted with the above buffer at 4° C. Fractions 18–20 (1.2 ml each, retained full enzymic activity) contains the title compound as determined by TLC, UV (at 280) and amino acid analysis.

In the second derivatization, β-glucocerebrosidase (3.7 mg, 1 ml; $3.7\times10^6$ units of enzymic activity) is subjected to more extensive reaction conditions: with reactants 5 (10 mg) and ECD (5 mg+3.5 mg after 24 hours) for 4 d at 4° C. After 24 hours, the modified enzyme is assayed for catalytic activity and reactive amino groups, and is formed to retain 70% enzyme activity and 50% of reactive amino groups compared to the native β-glucocerebrosidase. After 4 d, the reaction mixture is centrifuged and the supernatant is chromatographed as above to give the conjugate (37% protein recovery, 1.0×10⁶ units of enzymic activity).

What is claimed is:

1. A glycopeptide selected from compounds of the formula:

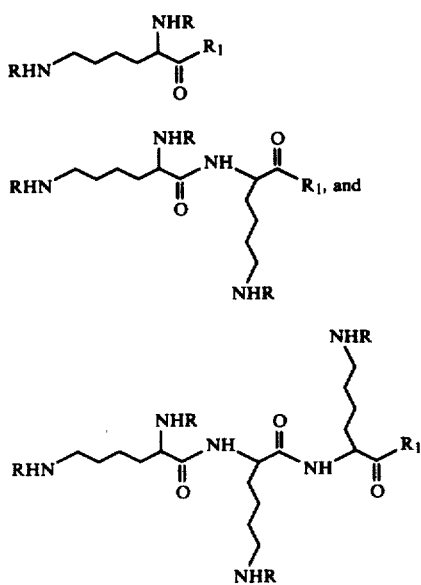

wherein R is a saccharide compound selected from the group consisting of

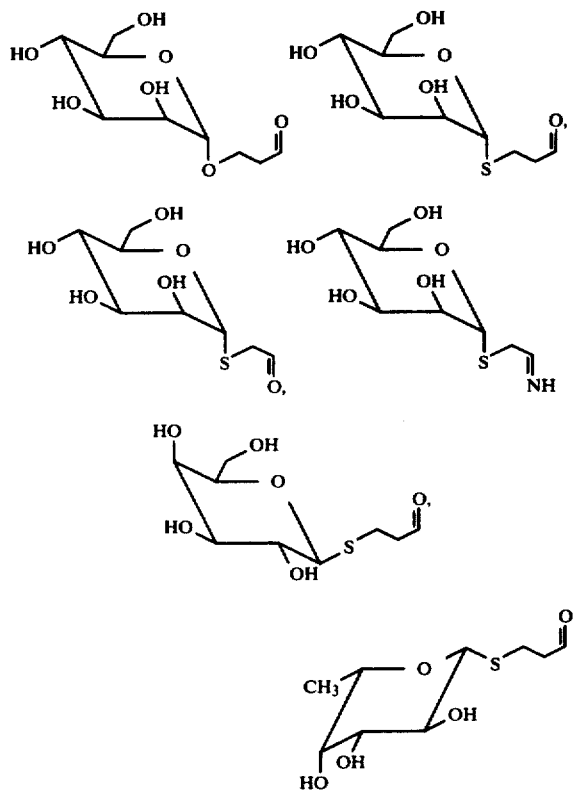

and $R_1$ is selected from the group consisting of hydroxyl and $NHR_2$ wherein $R_2$ is 6-aminohexyl and acid addition salts thereof.

2. A compound according to claim 1 selected from the group consisting of compounds $N^2$-{$N^2,N^6$-Bis-[3-(α-D-mannopyranosylthio)propionyl]-L-lysyl}-$N^6$-[3-(α-D-mannopyranosylthio)propionyl]-L-lysine, $N^2$-{$N^2,N^6$-Bis[1-imino-2-(α-D-mannopyranosylthio)ethyl]-L-lysyl}$N^6$-[1-imino-2-(α-D-mannopyranosylthio)ethyl]-L-lysine, N-6-Aminohexyl-$N^2$-{$N^2,N^6$-bis[3-(α-D-mannopyranosylthio)propionyl]-L-lysyl}-$N^6$-[3(α-D-mannopyranosylthio)propionyl]-L-lysinamide trifluoroacetate salt, $N^2,N^6$-Bis[3-(α-D-mannopyranosylthio)proionyl]-L-lysine, $N^2,N^6$-Bis[3-(α-D-mannopyranosylthio)propionyl]-D-lysine, $N^2$-{$N^2$-{$N^2,N^6$-Bis[3-(α-D-mannopyranosylthio)propionyl]-L-lysyl}-$N^6$-[3-(α-D-mannopyranosylthio)propionyl]-L-lysyl}-$N^6$-[3-(α-D-mannopyranosylthio)propionyl]-L-lysine, $N^2$-{$N^2,N^6$-Bis[3-(β-D-galactopyranosylthio)propionyl]-L-lysyl}-$N^6$-[3-(β-D-galactopyranosylthio)propionyl]-L-lysine, N-6-Aminohexyl-$N^2$-{$N^2,N^6$-bis[3-(β-D-galactopyranosylthio)propionyl]-L-lysyl}-$N^6$-[3-(β-D-galactopyranosylthio)propionyl]-L-lysinamide trifluoroacetate salt, $N^2$-{$N^2,N^6$-Bis[3-(β-L-fucopyranosylthio)propionyl]-L-lysyl}-$N^6$[3-(β-L-fucopyranosylthio)propionyl]-L-lysine, $N^2$-{$N^2,N^6$-Bis[(α-D-mannopyranosylthio)acetyl]-L-lysyl}-$N^6$-[(α-D-mannopyranosylthio)acetyl]-L-lysine, N-6-Aminohexyl-$N^2,N^6$-bis[3-(α-D-mannopyranosylthio)propionyl]-L-lysinamide trifluoroacetate salt, $N^2,N^5$-Bis[3-(α-D-mannopyranosylthio)propionyl]-L-ornithine, and Man⁹-Lys⁸.

3. A composition comprising a glvcopeptide as defined in claim 1 conjugated with a bioactive substance, selected from the group consisting of a drug, an enzyme a hormone, a genetic fragment, an antibiotic, or a radioactive isotope.

4. A composition according to claim 3 selected from the group consisting of compounds N-6-[3-(p-Hydroxyphenyl)propionamido]hexyl-$N^2$-{$N^2,N^6$-bis[3-(α-D-mannopyranosylthio)propionyl]-L-lysyl}-$N^6$-[3-(α-D-mannopyranosylthio)propionyl]-L-lysinamide, N-6-(6″-Deoxyraffinosyl)aminohexyl-$N^2$-{$N^2,N^6$-bis[3-(α-D-mannopyranosylthio)propionyl]-L-lysyl}-$N^6$-[3-(α-D-mannopyranosylthio)propionyl]-L-lysinamide, N-α-N$^α$,N$^ε$-Bis[3-(α-D-mannopyranosylthio)propionyl]-L-lysyl}-N-[6-(carboxyamino)hexyl]-N$^ε$-[3-(α-D-mannopyranosylthio)propionyl]-L-lysinamide, 21-ester with dexamethasone, $N^2$-{$N^2,N^6$-Bis[3-(α-D-mannopyranosylthio)propionyl]-L-lysyl}-$N^6$-[3-(α-D-mannopyranosylthio)propionyl]-L-lysine, 21-ester with dexamethasone, N-6-(5-Cholesten-3β-yloxy)hexyl-$N^2$-{$N^2,N^6$-bis[3-(α-D-mannopyranosylthio)propionyl-L-lysyl}$N^6$-[3-(α-D-mannopyranosylthio)propionyl-L-lysinamide, N-6-[3-(p-Hydroxyphenyl)propionamido]hexyl-$N^2,N^6$-bis[3-(α-D-mannopyranosylthio)propionyl]-L-lysinamide, and Man³Lys²-Glucocerebrosidase Conjugate.

5. A compound according to claim 3 which is $N^2$ $N^2,N^6$-Bis[3-($\alpha$-D-mannopyranosylthio)propionyl]-L-lysyl-$N^6$-[3-($\alpha$-D-mannopyranosylthio)propionyl]-L-lysine, 21-ester with dexamethasone (10A).

6. A compound according to claim 3 which is Man$^3$-Lys$^2$-glucocerebrosidase conjugate.

7. A per-o-acetylated glycopeptide according to claim 1 selected from compounds of the formula:

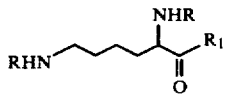

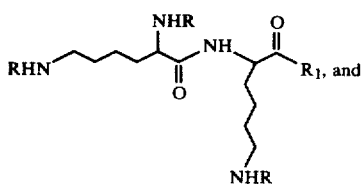

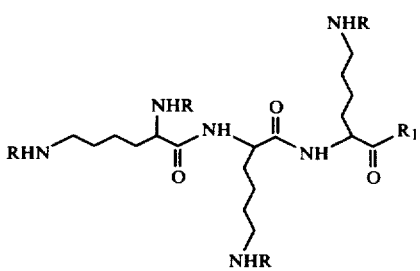

wherein R is a saccharide compound selected from the group consisting of:

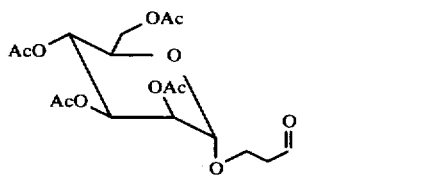

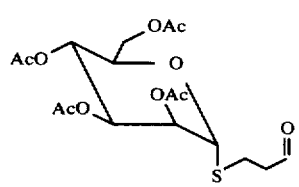

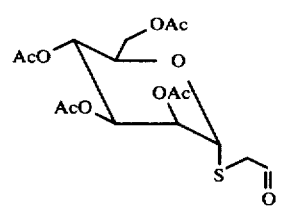

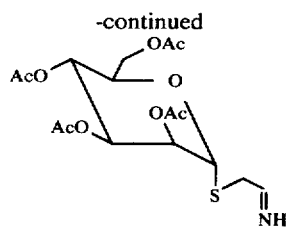

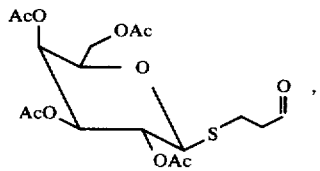

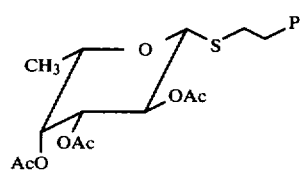

8. An intermediate compound according to claim 7 selected from the group consisting of compounds
$N^2$-{$N^2,N^6$-Bis[3-(2,3,4,6-tetra-O-acetyl-$\alpha$-D-mannopyranosylthio)propionyl]-L-lysyl}-$N^6$-[3-(2,3,4,6-tetra-O-acetyl-$\alpha$-D-mannopyranosylthio)propionyl]-L-lysine, N-6-t-Butyloxycarbonylaminohexyl-$N^2$-{$N^2,N^6$-bis[3-(2,3,4,6-tetra-O-acetyl-$\alpha$-D-mannopyranosylthio)-propionyl]-L-lysyl}-$N^6$-[3-(2,3,4,6tetra-O-acetyl-$\alpha$-D-mannopyranosylthio)propionyl]-L-lysinamide, $N^2N^6$-Bis[3-(2,3,4,6-tetra-O-acetyl-$\alpha$-D-mannopyranosylthio)propionyl]-L-lysine, $N^2,N^6$-Bis[3-(2,3,4,6-tetra-O-acetyl-$\alpha$-D-mannopyranosylthio)propionyl]-D-lysine, $N^2$-{$N^2$-{$N^2,N^6$-Bis[3-(2,3,4,6-tetra-O-acetyl-$\alpha$-D-mannopyranosylthio)propionyl]-L-lysyl}-$N^6$-[3-(2,3,4,6-tetra-O-acetyl-$\alpha$-D-mannopyranosylthio)propionyl]-L-lysyl}-$N^6$-[3-(2,3,4,6-tetra-O-acetyl-$\alpha$-D-mannopyranosylthio)propionyl]-L-lysine, $N^2$-{$N^2,N^6$-Bis[3-(2,3,4,6-tetra-O-acetyl-$\beta$-D-galactopyranosylthio)propionyl]-L-lysyl}-$N^6$-[3-(2,3,4,6-tetra-O-acetyl-$\beta$-D-galactopyranosyl)propionyl]-L-lysine, N-6-t-Butyloxycarbonylaminohexyl-$N^2$-{$N^2,N^6$-bis[3-(2,3,4,6-tetra-O-acetyl-$\beta$-D-galactopyranosylthio)-propionyl]-L-lysyl}-$N^6$-[3-(2,3,4,6-tetra-O-acetyl-$\beta$-D-galactopyranosylthio)propionyl]-L-lysinamide, $N^2$-{$N^2,N^6$-Bis[3-(2,3,4-tri-O-acetyl-$\beta$-L-fucopyranosylthio)propionyl]-L-lysyl}-$N^6$[3-(2,3,4-tri-O-acetyl-$\beta$-L-fucopyranosylthio)propionyl]-L-lysine, $N^2$-{$N^2,N^6$-Bis[(2,3,4,6-tetra-O-acetyl-$\alpha$-mannopyranosylthio)acetyl]-L-lysyl}-$N^6$-[(2,3,4,6-tetra-O-acetyl-$\alpha$-D-mannopyranosylthio)acetyl]-L-lysine, N-6-t-Butyloxycarbonylaminohexyl-$N^2,N^6$-bis[3-(2,3,4,6-tetra-O-acetyl-$\alpha$-D-mannopyranosylthio)-propionyl]-L-lysinamide, $N^2,N^5$-Bis[3-(2,3,4,6-tetra-O-acetyl-$\alpha$-D-mannopyranosylthio)propionyl]-L-ornithine, and Per O-acetyl-Man$^9$Lys$^8$.

* * * * *